(12) United States Patent
Kudo et al.

(10) Patent No.: US 7,402,250 B2
(45) Date of Patent: Jul. 22, 2008

(54) EQUIPMENT AND METHOD FOR FEEDING LIQUID GRADIENT IN NANO/MICRO LIQUID CHROMATOGRAPHY

(75) Inventors: Kenichi Kudo, Hachioji (JP); Yoshio Yamauchi, Hino (JP)

(73) Assignee: KYA Technologies Corporation, Hachioji-shi, Tokyo (JP)

( * ) Notice: Subject to any disclaimer, the term of this patent is extended or adjusted under 35 U.S.C. 154(b) by 763 days.

(21) Appl. No.: 10/509,440

(22) PCT Filed: Jul. 24, 2003

(86) PCT No.: PCT/JP03/09375

§ 371 (c)(1),
(2), (4) Date: Sep. 24, 2004

(87) PCT Pub. No.: WO2004/010134

PCT Pub. Date: Jan. 29, 2004

(65) Prior Publication Data

US 2005/0129539 A1    Jun. 16, 2005

(30) Foreign Application Priority Data

Jul. 24, 2002    (JP)    ............................ 2002-215415

(51) Int. Cl.
*B01D 15/08*    (2006.01)
(52) U.S. Cl. .................. 210/656; 210/659; 210/101; 210/143; 210/198.2
(58) Field of Classification Search ................ 210/635, 210/656, 659, 101, 137, 143, 416.1; 417/3, 417/4, 5, 6, 7, 8
See application file for complete search history.

(56) References Cited

U.S. PATENT DOCUMENTS 4,003,679 A  *  1/1977  McManigill ................. 417/246

(Continued)

FOREIGN PATENT DOCUMENTS

EP    0781995 A1    7/1997

(Continued)

OTHER PUBLICATIONS

Japanese Patent Abstract, Publication No. S50-71389, Published Jun. 13, 1975, Application No. S48-119686.

(Continued)

*Primary Examiner*—Ernest G Therkorn
(74) *Attorney, Agent, or Firm*—Rankin, Hill & Clark LLP

(57) ABSTRACT

It is an object of the present invention to improve the performance of gradient liquid transfer in nano/micro liquid chromatographs when solvents are mixed.

In a gradient liquid transfer device and method for a nano/micro liquid chromatograph, an opening and closing unit (160) capable of opening and closing a solvent passage (150) for transferring a secondary solvent is provided in the vicinity of a solvent mixing section (152) in a liquid transfer system (130); a passage from a metering pump (146) of a liquid transfer section (142) to the opening and closing unit (160) is filled with the secondary solvent in advance; and an appropriate pressure is applied to the secondary solvent. Therefore, the entry of a primary solvent into the solvent passage for transferring the secondary solvent is suppressed. In another gradient liquid transfer device and method for a nano/micro liquid chromatograph, a liquid having a low compression rate is filled, in advance, in a part of a solvent passage subsequent to a metering pump of a liquid transfer section, and only the required amount of a secondary solvent is filled subsequent to the liquid. Therefore, the entry of the primary solvent into a solvent passage for transferring the secondary solvent is suppressed, and liquid-transfer performance is improved.

3 Claims, 6 Drawing Sheets

U.S. PATENT DOCUMENTS

| | | | | |
|---|---|---|---|---|
| 4,032,445 | A | | 6/1977 | Munk |
| 4,133,767 | A | * | 1/1979 | Bakalyar et al. ............. 210/659 |
| 4,311,586 | A | * | 1/1982 | Baldwin et al. ............. 210/101 |
| 4,446,105 | A | * | 5/1984 | Dinsmore et al. ............. 422/70 |
| 4,534,659 | A | * | 8/1985 | Dourdeville et al. ........ 366/338 |
| 4,624,625 | A | * | 11/1986 | Schrenker .................... 417/20 |
| 4,840,730 | A | * | 6/1989 | Saxena .................... 210/198.2 |
| 4,942,018 | A | * | 7/1990 | Munk .......................... 422/70 |
| 5,080,785 | A | | 1/1992 | Allington et al. |
| 5,656,034 | A | | 8/1997 | Kochersperger et al. |
| 7,135,111 | B2 | * | 11/2006 | Deguchi et al. .......... 210/198.2 |
| 7,141,161 | B2 | * | 11/2006 | Ito ......................... 210/198.2 |
| 7,186,336 | B2 | * | 3/2007 | Gerhardt et al. .......... 210/198.2 |
| 7,332,087 | B2 | * | 2/2008 | Gerhardt et al. ............. 210/656 |
| 2005/0098487 | A1 | * | 5/2005 | Ito ............................. 210/101 |
| 2005/0109699 | A1 | * | 5/2005 | Gerhardt et al. ............. 210/659 |
| 2007/0034557 | A1 | * | 2/2007 | Ito ............................. 210/101 |

FOREIGN PATENT DOCUMENTS

| | | |
|---|---|---|
| WO | 96/30757 | 10/1996 |

OTHER PUBLICATIONS

Japanese Patent Abstract, Publication No. 53-044085, Published Apr. 20, 1978 "Liquid Chromatograph".

International Search Report for International Application No. PCT/JP03/09375.

* cited by examiner

EQUIPMENT AND METHOD FOR FEEDING LIQUID GRADIENT IN NANO/MICRO LIQUID CHROMATOGRAPHY

REFERENCE TO RELATED APPLICATIONS

This application is a 371 of PCT/JP03/09375 filed Jul. 24, 2003.

RELATED APPLICATIONS

The present application claims the benefit and priority of the Japanese Patent Application No. 2002-215415, filed in Japan on Jul. 24, 2002, the subject matter of which is hereby incorporated herein by reference.

BACKGROUND OF THE INVENTION

1. Field of the Invention

The present invention relates to gradient liquid transfer devices and methods for nano/micro liquid chromatographs, and more-particularly, to an improvement of liquid transfer performance in solvent mixing.

2. Prior Art

Recently, high performance liquid chromatographs have served as representative means for the separation and analysis of trace components. FIG. 4 shows an example structure of such a chromatograph. In a high performance liquid chromatograph 10, a solvent is transferred by a pump 14 from a mobile-phase solvent tank 12 through a passage, and an injector 16 introduces a trace sample into the solvent in the passage. The flow of the solvent leads the trace sample to a subsequent column 18. The trace sample is separated into components at a controlled temperature. The separated components are then detected by detection means 20, such as an absorbance detector. A computer 22 processes and analyzes A/D-converted detected signals, and also controls the conditions of the chromatograph.

Recently, a lower flow rate and a lower volume have been used to separate infinitesimal components at high resolution. Nano/micro liquid chromatographs which u se a flow rate of several tens of micro liters per minute to a nano liter per minute have been developed.

FIG. 5 shows a conventional liquid transfer system used for gradient elution in such a nano/micro liquid chromatograph. In the liquid transfer system 30, at a primary-solvent liquid transfer section 32, a primary solvent is replenished from a primary-solvent tank 34 to a metering pump 36, and then, a valve 38 is switched to transfer the primary solvent from the metering pump 36 through a primary-solvent passage 40 connected thereto.

At a secondary-solvent liquid transfer section 42, a secondary solvent is replenished from a secondary-solvent tank 44 to a metering pump 46, and then a valve 48 is switched to transfer the secondary solvent from the metering pump 46 through a secondary-solvent passage 50 connected thereto.

A three-way tee 52 (solvent mixing section) connected to the primary-solvent passage 40 and to the secondary-solvent passage 50 mixes the two solvents at a predetermined ratio. The mixed solvent is transferred to a subsequent separation system through a mixed-solvent passage 54. The mixing ratio of the two solvents is determined by the ratio of the flow rates specified by the metering pumps, and is controlled by a control section such as a computer. With the mixing ratio of the solvents being gradually changed, the mixed solvent is transferred to the subsequent separation system for gradient elution.

Due to the following two reasons, however, a considerable amount of the primary solvent enters the secondary-solvent passage 50 when only the primary solvent is transferred at a first stage.

First, since only a part (for example, from the pump 46 to the valve 48 in FIG. 5) of the passage 50 is initially filled with the secondary solvent, the primary solvent enters an empty part (for example, from the valve 48 to the three-way tee 52 in FIG. 5) of the passage 50, which has a considerable volume.

Secondly, the pressure of the liquid transfer system reaches, for example, as high as several tens of kilograms per square centimeters because of the resistance of the separation system, which is subsequent to the liquid transfer system. The primary solvent having a high pressure and entering the secondary-solvent passage 50 pushes the secondary solvent, which was previously stored at atmospheric pressure, to compress the secondary solvent. As a result, a further amount of the primary solvent enters the secondary-solvent passage. When water is used as the primary solvent and acetonitrile is used as the secondary solvent, acetonitrile is compressed due to the pressure of the water, and a considerable amount of volume contraction occurs. Since nano/micro liquid chromatographs have very small passage diameters and very small passage volumes, this solvent contraction also largely affects the entry of the primary solvent into the secondary-solvent passage.

When a considerable amount of the primary solvent enters the secondary-solvent passage in this way, even if the operations of the metering pumps are controlled such that the transfer of the primary solvent only is switched to the transfer of the mixed solvent at a predetermined time, actual switching is performed at a time later than the predetermined time, as shown in the graph of FIG. 6. In other words, it takes time for the pump 46 to push back the primary solvent which has entered the secondary-solvent passage 50, the secondary solvent cannot be mixed with the primary solvent during this time; and a time delay thus occurs. Therefore, the mixed solvent may be transferred to the separation column with a delay, so that separation is performed late; or analysis of the measurement results may be inaccurate, which is a problem.

SUMMARY OF THE INVENTION

The present invention has been made in consideration of the foregoing issues of the conventional technology. It is an object of the present invention to improve the performance of gradient liquid transfer in nano/micro liquid chromatographs when solvents are mixed.

The foregoing object is achieved in one aspect of the present invention through the provision of a gradient liquid transfer device for a nano/micro liquid chromatograph, provided with a primary-solvent liquid transfer section having a metering pump for transferring a primary solvent and a primary-solvent passage subsequent to the metering pump; at least one liquid transfer section having a metering pump for transferring one other solvent and a solvent passage subsequent to the metering pump; a solvent mixing section connected to the passages and to a mixed-solvent passage for passing a mixed solvent made by mixing the solvents supplied through the passages at a predetermined mixing ratio and for leading to a subsequent separation system; and a control section for controlling the mixing ratio of the mixed solvent transferred to the subsequent separation system, the gradient liquid transfer device including, in the vicinity of the solvent mixing section, opening and closing means capable of opening and closing the solvent passage for transferring the one other solvent.

In the gradient liquid transfer device for a nano/micro liquid chromatograph, a liquid connection section for connecting the primary-solvent liquid transfer section and the at least one liquid transfer section may be further included.

The foregoing object is achieved in another aspect of the present invention through the provision of a gradient liquid transfer device for a nano/micro liquid chromatograph, provided with a primary-solvent liquid transfer section having a metering pump for transferring a primary solvent and a primary-solvent passage subsequent to the metering pump; at least one liquid transfer section having a metering pump for transferring one other solvent and a solvent passage subsequent to the metering pump; a solvent mixing section connected to the passages and to a mixed-solvent passage for passing a mixed solvent made by mixing the solvents supplied through the passages at a predetermined mixing ratio and for leading to a subsequent separation system; and a control section for controlling the mixing ratio of the mixed solvent transferred to the subsequent separation system, the gradient liquid transfer device including first storing means formed of the metering pump in the at least one liquid transfer section and a part of the solvent passage subsequent to the metering pump and filled in advance with a liquid having a low compression rate; and second storing means formed of a part of the solvent passage subsequent to the first storing means and filled with a required amount of the one other solvent subsequent to the liquid in advance.

The foregoing object is achieved in still another aspect of the present invention through the provision of a gradient liquid transfer method for a nano/micro liquid chromatograph provided with a primary-solvent liquid transfer section having a metering pump for transferring a primary solvent and a primary-solvent passage subsequent to the metering pump; at least one liquid transfer section having a metering pump for transferring one other solvent and a solvent passage subsequent to the metering pump; and a solvent mixing section connected to the passages and to a mixed-solvent passage for passing a mixed solvent made by mixing the solvents supplied through the passages at a predetermined mixing ratio and for leading to a subsequent separation system, the nano/micro liquid chromatograph gradually changing the mixing ratio of the mixed solvent and transferring the mixed solvent to the subsequent separation system for gradient elution, and including, in the vicinity of the solvent mixing section, opening and closing means capable of opening and closing the solvent passage for transferring the one other solvent, and the gradient liquid transfer method including a first step of closing the opening and closing means, of filling, in advance, a passage from the metering pump of the at least one liquid transfer section to the opening and closing means with the one other solvent, and of applying an appropriate pressure to the one other solvent; a second step of transferring the primary solvent to the subsequent separation system from the primary-solvent liquid transfer section through the solvent mixing section; and a third step of opening the opening and closing means, of transferring the one other solvent to the solvent mixing section at a predetermined flow rate, and of transferring the mixed solvent having the predetermined mixing ratio of the primary solvent and the one other solvent to the subsequent separation system.

The gradient liquid transfer method may be configured such that the nano/micro liquid chromatograph further includes a liquid connection section for connecting the primary-solvent liquid transfer section and the at least one liquid transfer section, and pressure generated in the primary-solvent liquid transfer section in the second step is applied to the at least one liquid transfer section to apply the appropriate pressure to the one other solvent in the first step.

The foregoing object is achieved in yet another aspect of the present invention through the provision of a gradient liquid transfer method for a nano/micro liquid chromatograph provided with a primary-solvent liquid transfer section having a metering pump for transferring a primary solvent and a primary-solvent passage subsequent to the metering pump; at least one liquid transfer section having a metering pump for transferring one other solvent and a solvent passage subsequent to the metering pump; and a solvent mixing section connected to the passages and to a mixed-solvent passage for passing a mixed solvent made by mixing the solvents supplied through the passages at a predetermined mixing ratio and for leading to a subsequent separation system, the nano/micro liquid chromatograph gradually changing the mixing ratio of the mixed solvent and transferring the mixed solvent to the subsequent separation system for gradient elution, and the gradient liquid transfer method including a first step of filling, in advance, a liquid having a low compression rate in a part of the solvent passage subsequent to the metering pump of the at least one liquid transfer section; a second step of filling a required amount of the one other solvent, subsequent to the liquid, in the solvent passage; a third step of transferring the primary solvent to the subsequent separation system from the primary-solvent liquid transfer section through the solvent mixing section; and a fourth step of transferring the one other solvent to the solvent mixing section at a predetermined flow rate, and of transferring the mixed solvent having the predetermined mixing ratio of the primary solvent and the one other solvent to the subsequent separation system.

In any of the above-described gradient liquid transfer devices and methods, it is preferred that the metering pumps be syringe-type metering pumps, each transferring the entire solvent by pushing the syringe in a single stroke.

DESCRIPTION OF THE PREFERRED EMBODIMENTS

Figure 1:
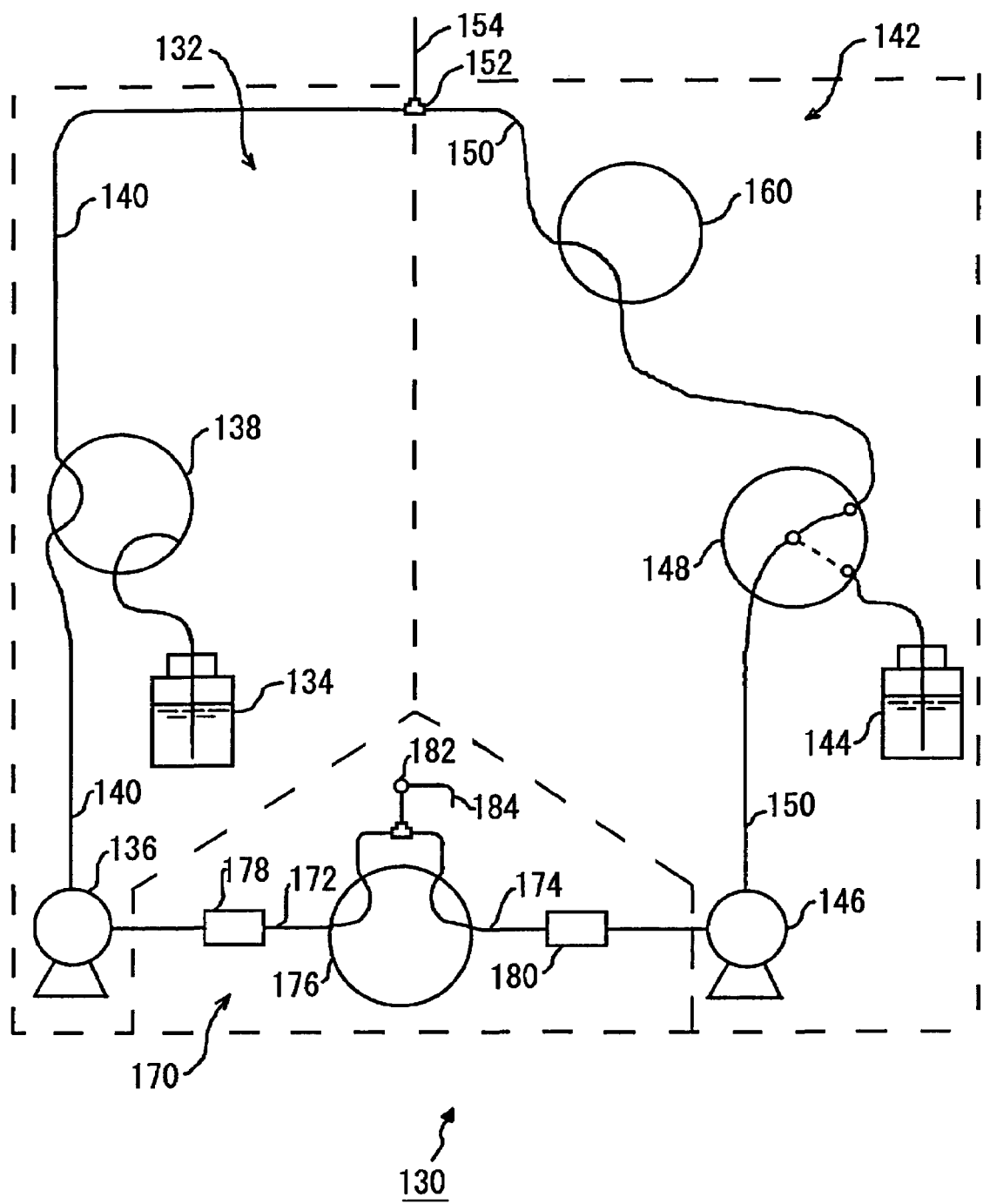
FIG. 1 is a view showing a liquid transfer system which employs a method according to a first embodiment of the present invention.

Embodiments of the present invention will be described below by referring to the drawings.

First Embodiment

FIG. 1 shows an outline structure of a liquid transfer system which employs a method according to a first embodiment of the present invention. Elements corresponding to those in the conventional technology have the same reference numerals as those assigned to the elements in the conventional technology plus 100. In the liquid transfer system 130, at a primary-solvent liquid transfer section 132, a primary solvent is replenished from a primary-solvent tank 134 to a metering pump 136, and then, a valve 138 is switched to transfer the primary solvent from the metering pump 136 through a primary-solvent passage 140 connected thereto.

At a secondary-solvent liquid transfer section 142, a secondary solvent is replenished from a secondary-solvent tank 144 to a metering pump 146, and then, a valve 148 is switched to transfer the secondary solvent from the metering pump 146 through a secondary-solvent passage 150 connected thereto.

In the present embodiment, capillaries having a passage diameter of 250 µm or smaller are used for the primary-solvent passage 140 and the secondary-solvent passage 150.

A three-way tee (solvent mixing section) 152 connected to the primary-solvent passage 140 and to the secondary-solvent passage 150 mixes the two solvents at a predetermined ratio. The mixed solvent is transferred to a subsequent separation system through a mixed-solvent passage 154. The mixing ratio of the two solvents is determined by the ratio of the flow rates specified by the metering pumps, and is controlled by a control section such as a computer. With the mixing ratio of the solvents being gradually changed, the mixed solvent is transferred to the subsequent separation system for gradient elution.

The present embodiment is characterized by providing, in the vicinity of the solvent mixing section 152, opening and closing means capable of opening and closing the solvent passage 150 which transfers the second solvent. In the present embodiment, a valve 160 is used as the opening and closing means. Since the opening and closing means is provided in the vicinity of the solvent mixing section 152, the entry of the primary solvent into the secondary-solvent passage 150, which is the problem described above, can be greatly suppressed. More specifically, the primary solvent can enter the secondary-solvent passage 150 just as far as the closest end of the valve 160, which is a small volume, and cannot enter the other part of the passage between the valve 160 and the metering pump 146, which occupies a relatively large volume. With the use of the opening and closing means, the method according to the present invention has the following steps.

First Step

The valve 160 is closed to block the passage 150, and the passage between the metering pump 146 and the valve 160 is filled with the secondary solvent. An appropriate pressure is given to the secondary solvent by driving the metering pump 146. With the pressure being applied in advance, as in this case, the volume contraction of the secondary solvent caused by the pressure of the primary solvent applied when the valve 160 is opened can be suppressed. Therefore, the amount of the primary solvent entering the passage 150 is reduced accordingly. The pressure being applied in advance to the secondary solvent is appropriately determined according to conditions such as the solvent used.

Second Step

The primary solvent is transferred from the primary-solvent liquid transfer section 132 to the subsequent separation system through the solvent mixing section 152. The pressure of the liquid transfer system gradually increases due to the resistance of the subsequent separation system. In the present embodiment, in order to quickly reach a high pressure (20 kg/cm², for example,), the primary solvent is transferred first at a rate of 500 µl/min, and later, when the high pressure is obtained, at a rate of 500 nl/min.

Third Step

The valve 160 is opened to transfer the secondary solvent to the solvent mixing section 152 at a predetermined flow rate. The mixed solvent having a predetermined mixing ratio of the primary solvent and the secondary solvent is transferred to the subsequent separation system. In the, present embodiment, the primary solvent entering the passage 150 is limited to a small volume as far as the valve 160, and in addition, since the pressure is given in advance to the secondary solvent, the entry of the primary solvent into the passage 150 caused by the compression of the secondary solvent is also suppressed. Therefore, a delay from the predetermined time when the transfer of the primary solvent only should be switched to the transfer of the mixed solvent can be reduced.

The present embodiment is further characterized by providing a liquid connection section 170 for connecting the primary-solvent liquid transfer section 132 and the secondary-solvent liquid transfer section 142. In the first step described above, it is necessary to drive the pump 146 to apply the pressure to the secondary solvent. When the liquid connection section 170 is provided, the pressure of the primary-solvent liquid transfer section 132 obtained after the transfer of the primary solvent is started is conveyed to the secondary-solvent liquid transfer section 142. Since the same pressure is applied to the secondary solvent filling the section from the pump 146 to the valve 160, there is no need to perform any special operation to obtain a pressure balance.

In the present embodiment, the liquid connection section 170 is provided with capillaries 172 and 174 for storing the two solvents, a valve 176, and pressure gages 178 and 180. The primary solvent is stored in advance in the capillary 172, and the secondary solvent is stored in advance in the capillary 174. Then, the primary solvent is transferred to the subsequent separation system from the primary-solvent liquid transfer section 132 through the solvent mixing section 152. The pressure of the primary-solvent liquid transfer section 132 is gradually increased until it reaches a high pressure (20 kg/cm², for example). When the valve 176 is opened, since the primary solvent and the secondary solvent make contact in the liquid connection section 170, the high pressure is conveyed to the second-solvent liquid transfer section 142, and the same pressure is applied to the secondary solvent filling the section up to the closed valve 160. Therefore, the same effect as in the first step described above is obtained.

Since the capillaries 172 and 174 have sufficient volumes, the boundary between the primary solvent and the secondary solvent does not reach the pump 146 or the passage connected thereto. In addition, these solvents are not mixed. Because the valve 160 is opened at the start of the third step, the valve 176 may be closed to block the passage, if necessary. It is also preferred that a drain 184 be connected to the valve 176 through a stop valve 182.

When three or more types of solvents are used, a liquid transfer section(s) for transferring one other solvent(s) can be connected to the solvent mixing section 152 in addition to the liquid transfer section 142. In this case, any two of a plurality of liquid transfer sections can be connected.

Pressure Gages

Figure 7:
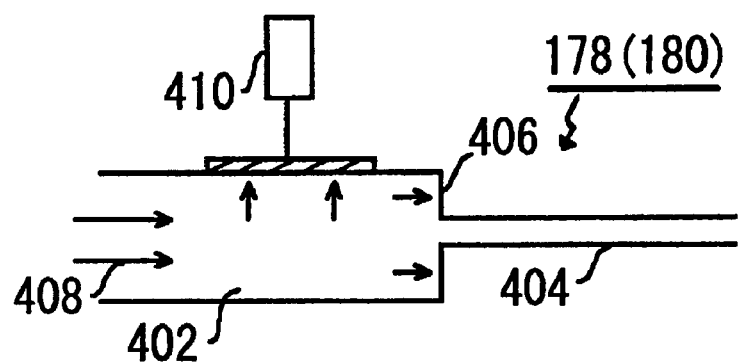
FIG. 7 is a view showing a pressure gage.

FIG. 7 shows an outline structure of the pressure gages 178 and 180 used in FIG. 1. In FIG. 7, when a mobile-phase solvent is transferred at a constant flow rate, the resistance of a wall surface 406 against the solvent flow occurs at a coupling section between a solvent passage 402 and a capillary 404. With this resistance, the pressure against the passage wall surfaces is increased around the coupling section due to the transfer of pressurized solvent in a flow direction 408. The increased pressure against the wall surfaces is detected by a pressure gage 410.

Since nano/micro liquid chromatographs use very small amounts of solvents, it is difficult to check whether the solvents are transferred correctly during measurement, more specifically whether the solvents are not leaked, or whether an extraordinarily high pressure due to clogging does not occur. Therefore, such a pressure gage is provided at the passage to monitor the liquid pressure to check whether the solvent is transferred correctly. More specifically, when the solvent is transferred correctly at a constant flow rate, a constant pressure is detected. If the solvent is leaked, such leakage is indicated by a pressure reduction. If an extraordinarily high pressure occurs due to clogging, it can be detected by the pressure gage.

Second Embodiment

Figure 2:
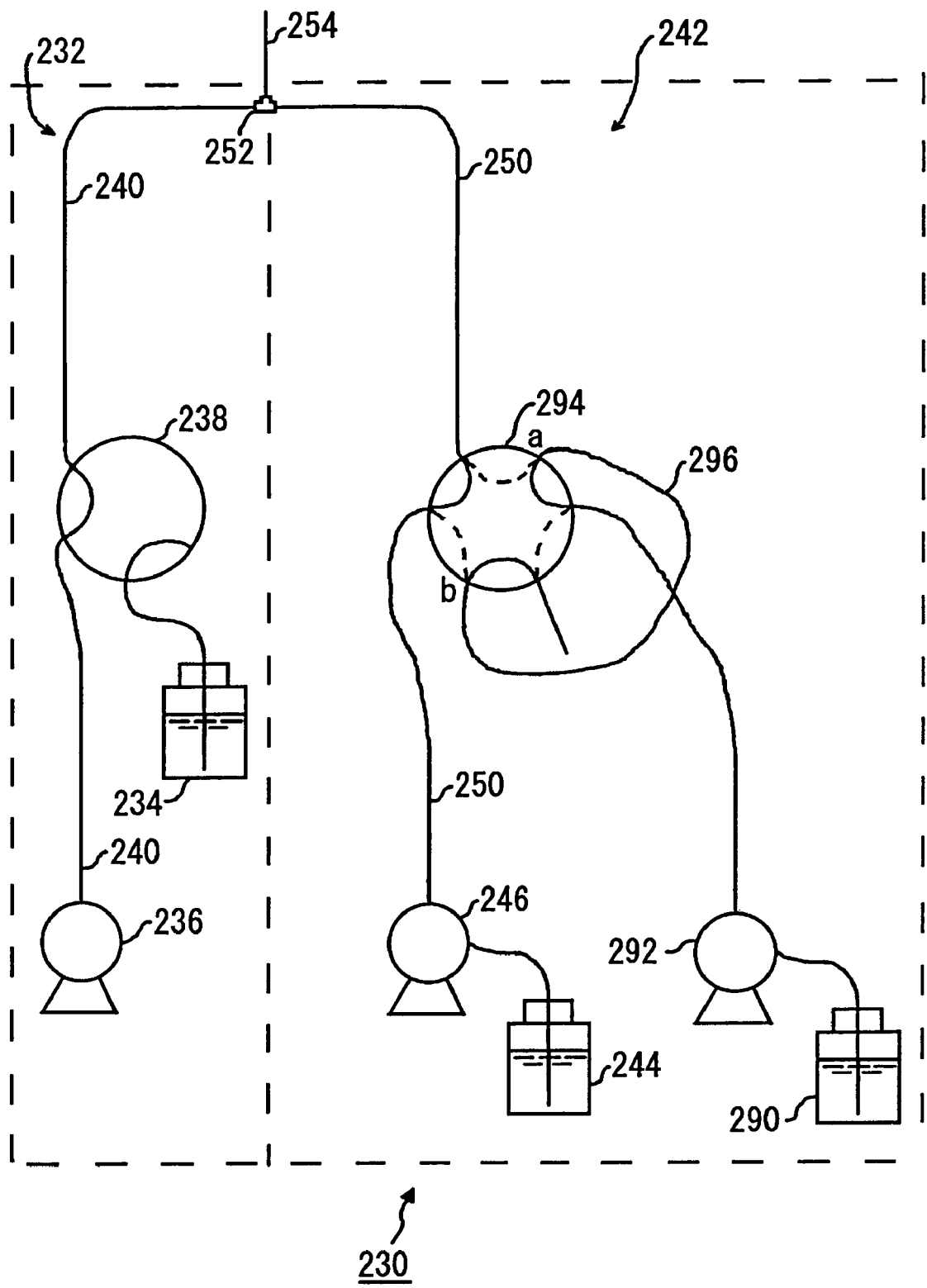
FIG. 2 is a view showing a liquid transfer system which employs a method according to a second embodiment of the present invention.

FIG. 2 shows an outline structure of a liquid transfer system which employs a method according to a second embodiment of the present invention. Elements corresponding to those in the first embodiment have the same reference numerals as those assigned to the elements in the first embodiment plus 100, and a description thereof is omitted.

The present embodiment is characterized in that a liquid having a low contraction rate with respect to pressure is filled, in advance, in a part of a solvent passage 250 subsequent to a metering pump 246 in a second-solvent liquid transfer section 242. With this liquid, the effect of the volume contraction of a secondary solvent caused by pressure is considerably suppressed. The liquid transfer method according to the present embodiment has the following steps.

First Step

The liquid having the low compression rate is filled, in advance, in the part of the solvent passage 250 subsequent to the metering pump 246. In FIG. 2, for example, a passage (first storing means) from the metering pump 246 to a six-way valve 294 is filled with such a liquid by using the metering pump 246 and a tank 244 which stores the liquid.

Second Step

The secondary solvent is transferred from a secondary-solvent tank 290 by a pump 292 to be filled, in advance, in a passage 296 (second storing means) between port "a" and port "b" of the six-way valve 294. The passage 296 needs to have a volume corresponding to the amount of the secondary solvent required for measurement. The six-way valve 294 is switched to paths indicated by dotted lines in FIG. 2 to fill the passage 250 with the secondary solvent following the liquid having the low compression rate.

Third Step

Figure 5:
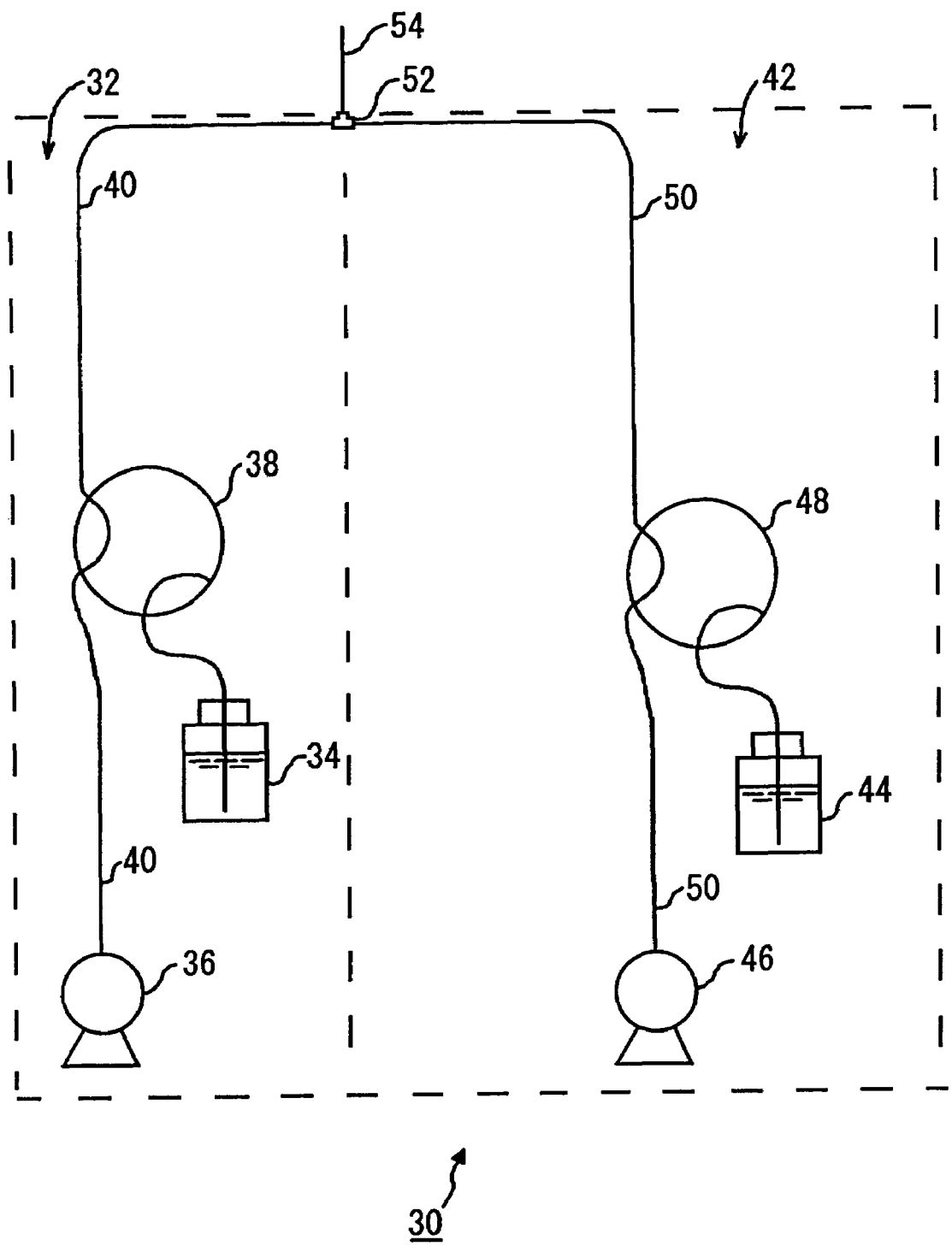
FIG. 5 is a view showing a conventional liquid transfer system.
Figure 6:
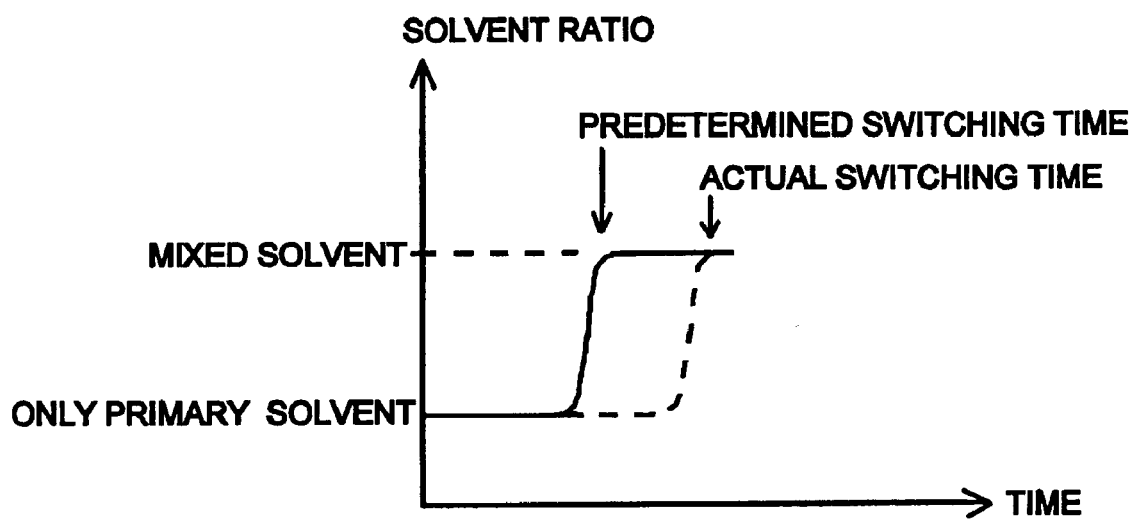
FIG. 6 is a view showing a switching time when the transfer of a primary solvent only is switched to the transfer of a mixed solvent.

A primary solvent is transferred from a primary-solvent liquid transfer section 232 to a subsequent separation system through a solvent mixing section 252. The pressure of the liquid transfer system gradually increases due to the resistance of the subsequent separation system. The primary solvent entering the passage 250 compresses the secondary solvent filled there in advance. However, since the passage from the pump 246 to the six-way valve 294 is filled with the liquid having the low compression rate, volume contraction can be suppressed in this passage having a relatively large volume. In other words, whereas, in the conventional technology shown in FIG. 5, the entire passage from the pump is filled with the secondary solvent and the secondary solvent is subjected to volume contraction due to pressure, in the present embodiment shown in FIG. 2, although the amount of the secondary solvent required for measurement is compressed, compression is only applied to that amount, and the entry of the primary solvent into the passage 250 caused by the volume contraction is considerably suppressed.

It is preferred that, as the liquid having the low compression rate, a liquid having a lower compression rate than the secondary solvent be appropriately selected according to other measurement conditions.

Fourth Step

The secondary solvent is transferred to the solvent mixing section 252 at a predetermined flow rate. The mixed solvent having a predetermined mixing ratio of the primary solvent and the secondary solvent is transferred to the subsequent separation system. As described above, since only the actual amount of the secondary solvent required for measurement is used in the present embodiment, a delay from a predetermined time when the transfer of the primary solvent only should be switched to the transfer of the mixed solvent can be reduced.

When three or more types of mobile-phase solvents are used, a liquid transfer section(s) for transferring one other solvent(s) can be connected to the solvent mixing section 252 in addition to the liquid transfer section 242.

Metering Pump

Figure 3:
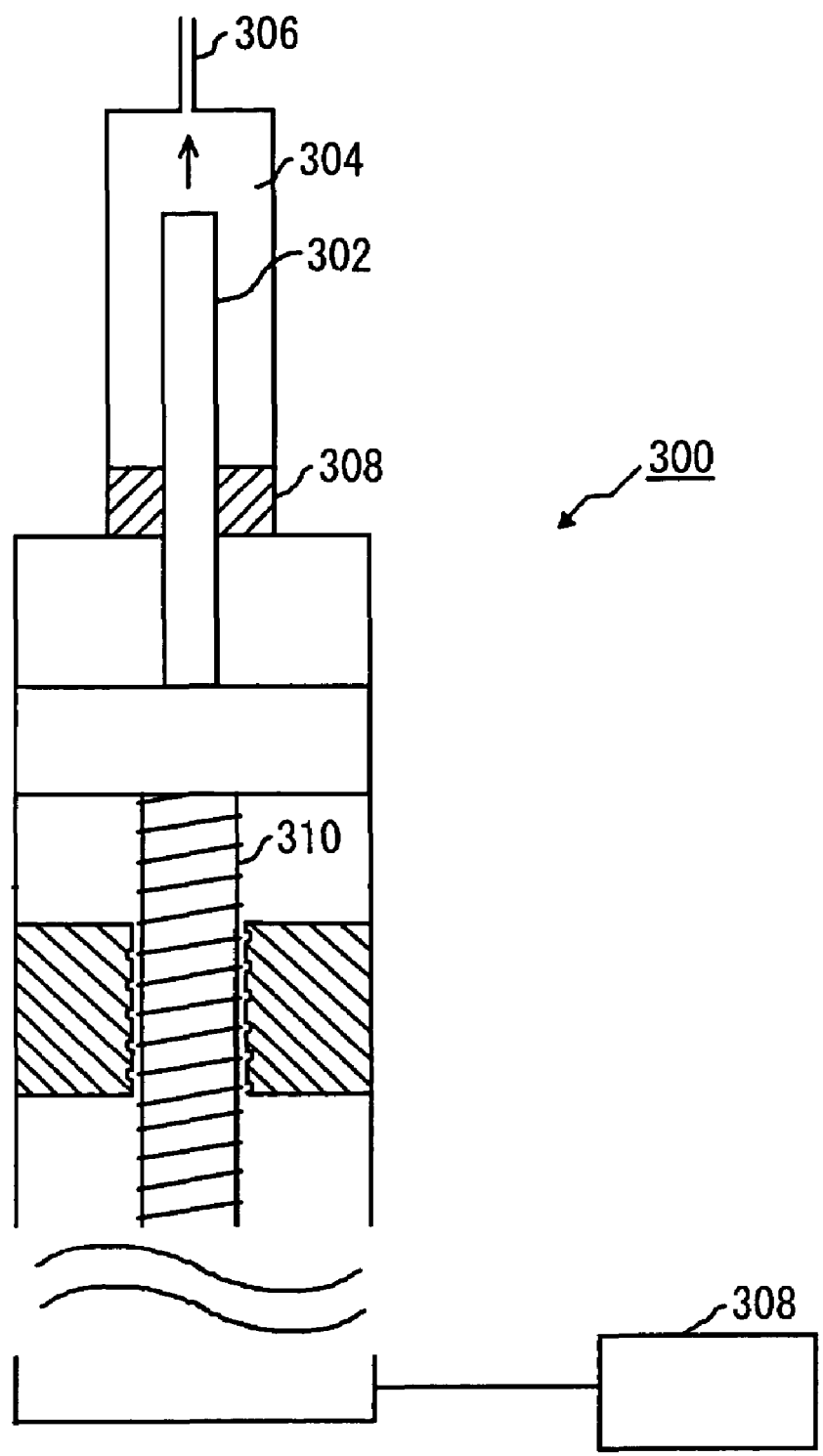
FIG. 3 is a view showing a syringe pump used in a method according to the present invention.
Figure 4:
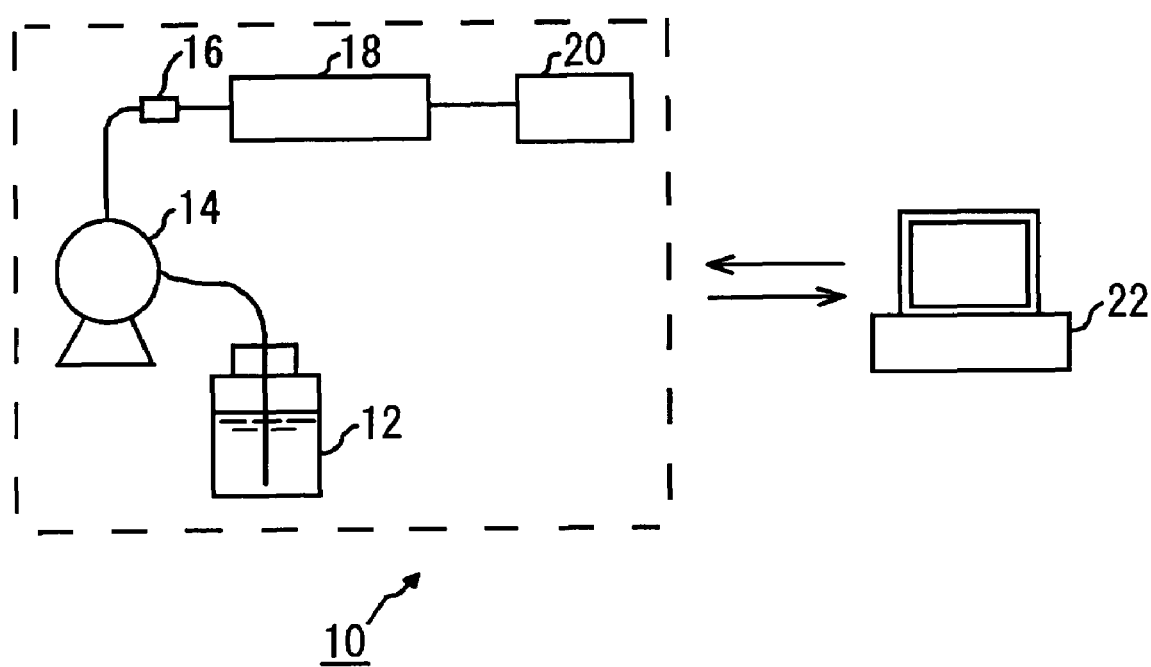
FIG. 4 is a view showing a high performance liquid chromatograph.

A syringe pump preferably used as a metering pump in the present invention will be described below by referring to FIG. 3. In a syringe pump 300 shown in FIG. 3, a solvent introduced in advance into a head 304 is discharged to a passage 306 by driving a syringe 302. Since nano/micro liquid chromatographs use a trace amount of a solvent for separation, the entire solvent is transferred by pushing the syringe in a single stroke with the use of the rotation of a screw 310 driven by a motor 308. Therefore, the transfer is performed without generating a pulsating flow caused by the repetitions of discharges and suctions.

When such a syringe pump is used, a temperature change of the pump may cause a change in the flow rate. Therefore, it is preferred that means for maintaining a constant temperature of the pump be used.

Even when appropriate temperature adjustment means is used, however, a change in the flow rate caused by the temperature change of the pump cannot be ignored in some cases. In our examination, it is found that, in order to suppress a change in the flow rate, it is effective to reduce the volume of the syringe introduced into the head 304 always while it is transferring liquid.

It is thought that the reason why the temperature change of the pump causes a change in the flow rate is a variation in the solvent volume caused by the temperature change of the pump, or a variation in the syringe volume, or both. The density of a solvent is increased by about 0.1% as the temperature increases by 1° C. The volume of the syringe may also increase with temperature. Therefore, reducing the volume of the syringe should reduce those variations. It is especially preferred that the volume be set to 1000 μl or smaller.

As described above, according to a gradient liquid transfer device and method of the present invention, the following advantages are obtained.

(1) The opening and closing means capable of opening and closing the secondary-solvent passage is provided in the vicinity of the solvent mixing section; the passage from the metering pump of the secondary-solvent liquid transfer section to the opening and closing means is filled with the secondary solvent in advance; and an appropriate pressure is applied to the secondary solvent. Therefore, the entry of the primary solvent into the secondary-solvent passage is suppressed. In this case, when the liquid connection section for connecting the primary-solvent liquid transfer section and the secondary-solvent liquid transfer section is provided, since the pressure of the primary solvent is applied to the secondary solvent, an operation for applying an appropriate pressure to the secondary solvent can be omitted.

(2) The liquid having the low compression rate is filled, in advance, in a part of the solvent passage subsequent to the metering pump of the liquid transfer section, and only the required amount of the secondary solvent is filled subsequent to the liquid. Therefore, the entry of the primary solvent into the secondary-solvent passage is suppressed.

What is claimed is:

1. A gradient liquid transfer method for a nano/micro liquid chromatograph provided with: a primary-solvent liquid transfer section having a metering pump for transferring a primary solvent and a primary-solvent passage subsequent to the metering pump; at least one liquid transfer section having a metering pump for transferring one other solvent and a solvent passage subsequent to the metering pump; and a solvent mixing section connected to the passages and to a mixed-solvent passage for passing a mixed solvent made by mixing the solvents supplied through the passages at a predetermined mixing ratio and for leading to a subsequent separation system, the nano/micro liquid chromatograph gradually changing the mixing ratio of the mixed solvent and transferring the mixed solvent to the subsequent separation system for gradient elution, and comprising, in the vicinity of the solvent mixing section, opening and closing means capable of opening and closing the solvent passage for transferring the one other solvent, and the gradient liquid transfer method comprising: a first step of closing the opening and closing means, of filling, in advance, a passage from the metering pump of the at least one liquid transfer section to the opening and closing means with the one other solvent, and of applying an appropriate pressure to the one other solvent; a second step of transferring the primary solvent to the subsequent separation system from the primary-solvent liquid transfer section through the solvent mixing section; and a third step of opening the opening and closing means, of transferring the one other solvent to the solvent mixing section at a predetermined flow rate, and of transferring the mixed solvent having the predetermined mixing ratio of the primary solvent and the one other solvent to the subsequent separation system.

2. A gradient liquid transfer method for a nano/micro liquid chromatograph according to claim 1, the nano/micro liquid chromatograph further comprising a liquid connection section for connecting the primary-solvent liquid transfer section and the at least one liquid transfer section, wherein pressure generated in the primary-solvent liquid transfer section in the second step is applied to the at least one liquid transfer section to apply the appropriate pressure to the one other solvent in the first step.

3. A gradient liquid transfer method for a nano/micro liquid chromatograph according to claim 1 wherein the metering pumps are syringe-type metering pumps, each transferring the entire solvent by pushing the syringe in a single stroke.

* * * * *